(12) United States Patent
Tatemoto

(10) Patent No.: US 6,649,790 B1
(45) Date of Patent: Nov. 18, 2003

(54) PROCESS FOR PRODUCING PERFLUORO (VINYL ETHER) SULFONIC ACID DERIVATIVE

(75) Inventor: Masayoshi Tatemoto, Takatsuki (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/111,079

(22) PCT Filed: Oct. 19, 2000

(86) PCT No.: PCT/JP00/07266

§ 371 (c)(1),
(2), (4) Date: Apr. 19, 2002

(87) PCT Pub. No.: WO01/28989

PCT Pub. Date: Apr. 26, 2001

(30) Foreign Application Priority Data

Oct. 19, 1999 (JP) .......................................... 11-296639

(51) Int. Cl.⁷ ............................................ C07C 309/02
(52) U.S. Cl. ...................................... 562/111
(58) Field of Search ............................. 562/30, 108, 110, 562/111, 113

(56) References Cited

U.S. PATENT DOCUMENTS 4,358,412 A    11/1982  Ezzell et al.
5,374,770 A  * 12/1994  Navarrini et al. ........... 562/111
6,274,677 B1 *  8/2001  Tatemoto ..................... 525/276
6,403,539 B1 *  6/2002  Marchionni et al. ........ 508/406

FOREIGN PATENT DOCUMENTS

WO    WO98/43952    10/1998

* cited by examiner

*Primary Examiner*—Jean F. Vollano
(74) *Attorney, Agent, or Firm*—Larson & Taylor PLC

(57) ABSTRACT

A process for preparing a monomer compound represented by formula (II):

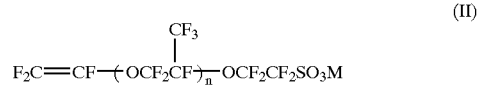

(II)

[wherein M represents an alkali metal or alkaline earth metal; and n is 0, 1 or 2.] by pyrolysis of a compound represented by formula (I) below:

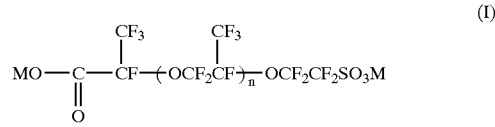

(I)

[wherein M and n are as defined above.], the pyrolysis being conducted in the presence of a catalyst which has coordinating properties to a metal ion M.

10 Claims, No Drawings

PROCESS FOR PRODUCING PERFLUORO (VINYL ETHER) SULFONIC ACID DERIVATIVE

This application is a 371 of PCT/JP00/07266, filed Oct. 19, 2000, now WO 01/28989.

TECHNICAL FIELD

The present invention relates to an efficient process for producing a perfluorovinyl ethersulfonic acid derivative represented by formula (II) below:

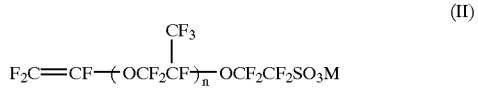
(II)

[wherein M represents an alkali metal or ½(alkaline earth metal); n is 0, 1 or 2.]

BACKGROUND ART

Known fluorine-based ionomers include copolymers which have a perfluoro polymer chain and a sulfonate group or carboxyl group bonded thereto, such as Nafion®, Flemion®, etc. These ionomers have been developed chiefly as ion-exchange membranes for use in electrolysis of sodium chloride. Researchers are also studying their uses as chemical sensors, separation membranes, polymeric superacid catalysts, polyelectrolytes for conducting protons in fuel cells, among others.

It is known that perfluorovinyl ethersulfonic acid derivatives (II), which are raw materials for these fluorine-based ionomers, can be prepared by pyrolysis of a corresponding starting compound (I) according to the scheme below (refer to WO98/43952 pamphlet).

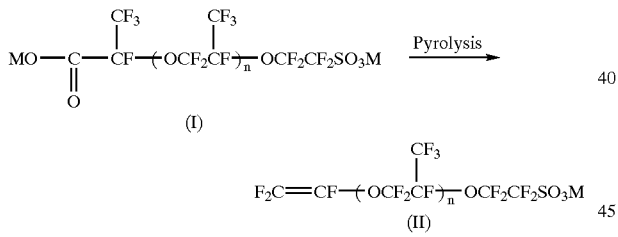

[wherein M and n are as defined above.]

However, the above pyrolysis has the following problem: if the heating time is too short, the starting compound remains in the product, whereas if the heating time is too long, by-products such as oligomers which are further polymerized substances of the desired product and compounds represented by formula (III) below

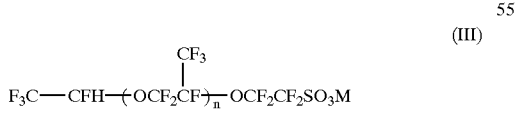
(III)

[wherein M and n are as defined above.] and the like. Because a large amount of the starting compound (I) requires considerable time for reaction and post-treatment, the remaining starting compound and generation of by-products are especially problematic.

An object of the present invention is to provide a process for preparing the monomer compound represented by formula (II)

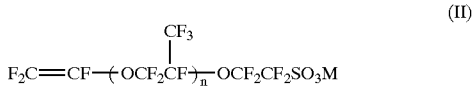
(II)

[wherein M and n are as defined above.] in a high yield.

DISCLOSURE OF THE INVENTION

The inventors of the present invention conducted extensive research on the above problems. Consequently, they found that conducting pyrolysis in the presence of a catalyst which has coordinating properties to a metal ion M, such as diglyme, can promote the reaction, inhibit remaining of raw materials and generation of by-products.

The present invention provides the following processes for preparing a perfluorovinyl ethersulfonic acid derivative.

Item 1: A process for preparing a perfluorovinyl

(II)

ethersulfonic acid derivative represented by formula (II): [wherein M represents an alkali metal or alkaline earth metal; and n is 0, 1 or 2.] by pyrolysis of a compound represented by formula (I) below:

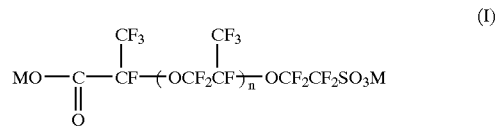
(I)

[wherein M and n are as defined above.], the pyrolysis being conducted in the presence of a catalyst which has coordinating properties to a metal ion M.

Item 2: The process of item 1 for preparing a perfluorovinyl ethersulfonic acid derivative represented by formula (II):

(II)

[wherein M represents an alkali metal or alkaline earth metal; and n is 0, 1 or 2.] by pyrolysis of a compound represented by formula (I) below:

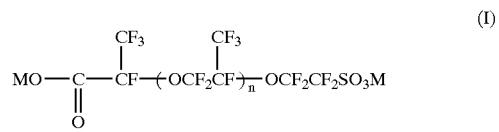
(I)

[wherein M and n are as defined above.] in an inert solvent, the pyrolysis being conducted in the presence of a catalyst which has coordinating properties to a metal ion M.

Item 3: The preparation process of item 1, wherein the catalyst which has coordinating properties to a metal ion M is a glyme-based compound.

Item 4: The preparation process of item 3, wherein the glyme-based compound is at least one member selected from the group consisting of diethylene glycol dimethyl ether, diethylene glycol diethyl ether, dimethoxyethane, diethoxyethane, tetraglyme and crown ether.

Item 5: The preparation process of item 4, wherein the glyme-based compound is diglyme.

Item 6: The preparation process of item 1, wherein n=0.

Item 7: The preparation process of item 1, wherein the catalyst which has coordinating properties to a metal ion M is added in an amount of about 0.1 to about 1000 parts by weight relative to 100 parts by weight of a starting compound represented by formula (I).

Item 8: The preparation process of item 1, wherein the catalyst which has coordinating properties to a metal ion M is added in an amount of about 0.1 to about 10 parts by weight relative to 100 parts by weight of a starting compound represented by formula (I).

Item 9: The preparation process of item 1, wherein M is an alkali metal.

Item 10: The preparation process of item 1, wherein M is sodium.

The starting compound represented by formula (I) used in the process of the present invention is a known one, and can be produced, for example, by the process disclosed in WO98/43952 pamphlet.

A process for preparing the starting compound represented by formula (I) is described below.

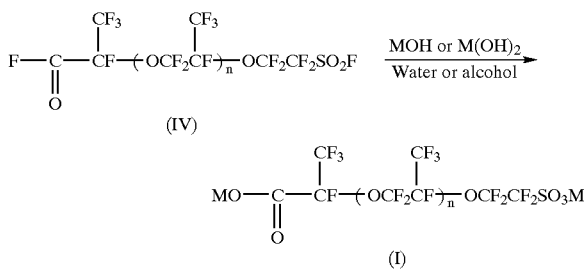

[wherein M and n are as defined above; and MOH is used when M is an alkali metal or M(OH)$_2$ is used when M is an alkaline earth metal.]

The compound of formula (I) can be obtained by dissolving or suspending 1 mole of the starting compound of formula (IV) in water or alcohol (methanol, ethanol, etc.) and allowing the mixture to react in the presence of 2 equivalents to an excess amount of MOH (NaOH, KOH, LiOH, CsOH, etc.) or M(OH)$_2$ (Ca(OH)$_2$, Mg(OH)$_2$, Ba(OH)2, etc.) at a temperature of about 20 to 80° C. for 1 to 24 hours.

The starting compound represented by formula (IV) is disclosed in WO98/43952.

Examples of catalysts which has coordinating properties to a metal ion M include glyme-based compounds such as diethylene glycol dimethyl ether (diglyme), diethylene glycol diethyl ether, dimethoxyethane, diethoxyethane, tetraglyme and crown ether, dioxane, dimethyl acetamide, dimethyl sulfoxide, among others. Examples also include alcohol-, ester- and ketone-based compounds. In the present invention, glyme-based compounds are hydrocarbon-type ether compounds which are represented by the following formula:

(wherein R represents $C_mH_{2m+1}$; m is 1 to 5; and n is 1 to 10.)

The starting compound may be subjected to pyrolysis in the solid state, or after being dispersed or dissolved in a solvent. When the starting compound is dispersed or dissolved in a solvent, the solvent used may be the above-mentioned catalyst itself or an inert liquid. Because it is difficult to completely dehydrate catalysts which have coordinating properties to a metal ion, preferable inert solvents are fluorocarbons which can be dehydrated relatively easily.

In the present invention, preferable inert solvents used in pyrolysis are, but are not limited to, fluorocarbons which have been perfluorinated, perfluorochlorinated or partially hydrogenated or etherified. Specifically, solvents having a boiling point of 200° C. or higher are preferable. Examples include $Cl(CF_2CFCl)_{m1}Cl$ (m1=3 or 4), $CF_3[OCF(CF_3)CF_2]_{m2}F$ (m2=6 to 8).

n is 0, 1 or 2, preferably 0 or 1, more preferably 0.

When pyrolysis is conducted in an inert solvent, the amount of the catalyst which has coordinating properties to a metal ion M is preferably about 0.1 to about 1000 parts by weight, more preferably about 0.1 to about 10 parts by weight, particularly preferably about 1 to about 5 parts by weight, relative to 100 parts by weight of the starting compound represented by formula (I). This catalyst may be used in a large amount. In this case, the amount of the catalyst is about 200 to 1000 parts by weight, preferably about 200 to 300 parts by weight, relative to 100 parts by weight of the starting compound. When the catalyst itself is used as a solvent, the amount of the catalyst is about 500 to 1000 parts by weight relative to 100 parts by weight of the starting compound.

The term "metal ion M" denotes an alkali metal ion such as $Na^+$, $K^+$, $Li^+$, $Cs^+$ and the like or an alkaline earth metal ion such as ½ $Ca^{2+}$, ½ $Mg^{2+}$ and the like.

In the present invention, pyrolysis is conducted generally at about 100° C. or higher, preferably about 150° C. to about 250° C., particularly preferably about 170 to about 230° C. In order to limit the generation of by-products, it is advantageous to complete the reaction at about 170° C. or higher in a short period of time.

Preferable reaction time is 10 to 120 minutes after a predetermined reaction temperature has been reached. The atmosphere inside the reaction system is preferably replaced with an inert gas such as nitrogen, argon, etc.

A preferable embodiment comprises the following steps: continuously feeding a mixture of the starting compound represented by formula (I), an inert solvent and a catalyst which has coordinating properties to a metal ion M into a cylindrical reactor whose temperature is controlled to about 170° C. to about 230° C.; heating the mixture for a certain period of time; drawing the reaction liquid from the reactor; cooling the reaction liquid; separating and collecting the reaction products from the solvent; and reusing the solvent.

The process of the present invention is preferably conducted under anhydrous conditions, and the starting compound (I), inert solvent, catalyst which has coordinating properties to a metal ion M and other materials used in the reaction are preferably anhydrous.

According to the present invention, the perfluorovinyl ethersulfonic acid derivative of formula (II), which is a raw material for strongly acidic fluorine-based polyelectrolyte, can be obtained in a high field while inhibiting the generation of by-products.

BEST MODE FOR CARRYING OUT THE INVENTION

The present invention will be explained in further detail referring to Examples and Comparative Examples below.

EXAMPLE 1

In a 1-liter flask equipped with a stirring blade, thermometer, nitrogen gas ($N_2$ gas) inlet and reflux condenser were placed 300 g of Cl(CF$_2$CFCl)$_3$Cl which has been newly purified by rectification and 4 g of dehydrated diglyme. A dry N$_2$ gas was introduced to the flask at a rate of 50 ml/min with stirring. Simultaneously, 240 g of a NaOCOCF(CF$_3$)OCF$_2$CF$_2$SO$_3$Na powder which has been heated and dried at 130° C. for 2 hours was placed in the flask carefully and quickly so that the powder did not absorb moisture. Immediately thereafter, the mixture was heated with a heating mantle. It was seen that reflux started after 20 minutes when the temperature reached 200° C. and after 5 more minutes the amount of the gas discharged from the reflux condenser suddenly increased. After continuing the reaction for about 20 minutes, the generation of gas almost stopped. Then, the heating mantle was turned off and the flask was rapidly cooled to room temperature in an ice bath for 5 minutes. The maximum reaction temperature was 207° C.

A brown granular powder dispersed in Cl(CF$_2$CFCl)$_3$Cl was filtrated with a glass filter. The powder was washed with a small amount of CF$_3$CHCl$_2$ and air-dried, giving a slightly colored granular powder. Then, the granular powder was dissolved in 200 ml of deionized water. After the pH of the solution was adjusted to 7 with a 10% aqueous solution of NaOH, the solution was filtrated again to collect a filtrate. The white residue remained on the filter was NaF. The filtrate was placed in an evaporator to evaporate water therein. When the entire filtrate became almost solid but wet, it was cooled in a refrigerator at 5° C. for 1 hour. The filtrate was then placed on a glass filter and filtrated in an atmosphere under reduced pressure at room temperature. A brown liquid gradually oozed out through the filter and a white crystalline powder remained on the filter. The $^{19}$F-NMR analysis of the white crystalline powder revealed that the powder was substantially the desired product, CF$_2$=CFOCF$_2$CF$_2$SO$_3$Na, which contained almost no oligomers of CF$_3$CFHOCF$_2$CF$_2$SO$_3$Na or CF$_2$=CFOCF$_2$CF$_2$SO$_3$Na. The amount of CF$_2$=CFOCF$_2$CF$_2$SO$_3$Na obtained was 155 g and the yield was 83%.

COMPARATIVE EXAMPLE 1

Pyrolysis was conducted in the same manner as in Example 1 except that diglyme was not used in the reaction. The $^{19}$F-NM analysis of the product revealed that the desired product, CF$_2$=CFOCF$_2$CF$_2$SO$_3$Na, was obtained in an approximately 20% yield; the raw material, NaOCOCF(CF$_3$)OCF$_2$CF$_2$SO$_3$Na, remained in the mixture after the completion of the reaction but before being cooled; and a large amount of by-products, oligomers of CF$_3$CFHOCF$_2$CF$_2$SO$_3$Na and CF$_2$=CFOCF$_2$CF$_2$SO$_3$Na were generated.

Because the raw material and oligomers have low crystallizabilities, they could be removed from the obtained reaction mixture by crystallization of the reaction mixture in the same post-treatment as in Example 1. However, the $^{19}$F-NMR analysis of crystals of the desired product indicated that the obtained product contained CF$_2$=CFOCF$_2$CF$_2$SO$_3$Na as a main component and a small amount of CF$_3$CFHOCF$_2$CF$_2$SO$_3$Na as a by-product.

What is claimed is:

1. A process for preparing a perfluorovinyl ethersulfonic acid derivative represented by formula (II):

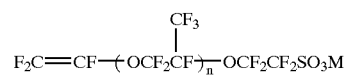
(II)

[wherein M represents an alkali metal or alkaline earth metal; and n is 0, 1 or 2] by pyrolysis of a compound represented by formula (I) below:

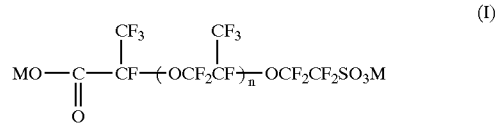
(I)

[wherein M and n are as defined above.], the pyrolysis being conducted in the presence of a catalyst which coordinates to a metal ion M.

2. The process of claim 1 for preparing a perfluorovinyl ethersulfonic acid derivative represented by formula (II):

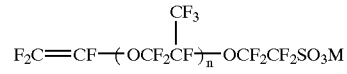
(II)

[wherein M represents an alkali metal or alkaline earth metal; and n is 0, 1 or 2] by pyrolysis of a compound represented by formula (I) below:

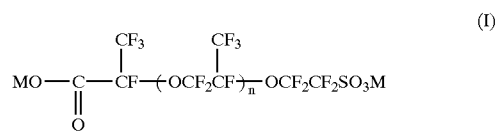
(I)

[wherein M and n are as defined above] in an inert solvent, the pyrolysis being conducted in the presence of a catalyst which coordinates to a metal ion M.

3. The preparation process of claim 1, wherein the catalyst which coordinates to a metal ion M is a glyme-based compound.

4. The preparation process of claim 3, wherein the glyme-based compound is at least one member selected from the group consisting of diethylene glycol dimethyl ether, diethylene glycol diethyl ether, dimethoxyethane, diethoxyethane, tetraglyme and crown ether.

5. The preparation process of claim 3, wherein the glyme-based compound is diglyme.

6. The preparation process of claim 1 wherein n=0.

7. The preparation process of claim 1, wherein the catalyst which coordinates to a metal ion M is added in an amount of about 0.1 to about 1000 parts by weight relative to 100 parts by weight of a starting compound represented by formula (I).

8. The preparation process of claim 1, wherein the catalyst which coordinates to a metal ion M is added in an amount of about 0.1 to about 10 parts by weight relative to 100 parts by weight of a starting compound represented by formula (I).

9. The preparation process of claim 1, wherein M is an alkali metal.

10. The preparation process of claim 1, wherein M is sodium.

* * * * *